United States Patent
Sparsø

(10) Patent No.: US 8,247,199 B2
(45) Date of Patent: Aug. 21, 2012

(54) PROCESS FOR PREPARING GLYCEROL ESTERS

(75) Inventor: Flemming Vang Sparsø, Brabrand (DK)

(73) Assignee: Dupont Nutrition Biosciences ApS, Copenhagen (DK)

( * ) Notice: Subject to any disclaimer, the term of this patent is extended or adjusted under 35 U.S.C. 154(b) by 366 days.

(21) Appl. No.: 12/522,130

(22) PCT Filed: Dec. 11, 2007

(86) PCT No.: PCT/IB2007/004381
§ 371 (c)(1),
(2), (4) Date: Dec. 3, 2009

(87) PCT Pub. No.: WO2008/081332
PCT Pub. Date: Jul. 10, 2008

(65) Prior Publication Data
US 2010/0143987 A1    Jun. 10, 2010

(30) Foreign Application Priority Data
Jan. 3, 2007    (GB) .................................. 0700074.8

(51) Int. Cl.
| | |
|---|---|
| C12P 7/62 | (2006.01) |
| C08L 91/00 | (2006.01) |
| C08K 5/00 | (2006.01) |
| A23D 9/00 | (2006.01) |
| C07C 239/00 | (2006.01) |

(52) U.S. Cl. ........ 435/135; 524/313; 524/312; 554/227; 560/312

(58) Field of Classification Search .................. 435/135; 524/313, 312; 554/227; 560/312
See application file for complete search history.

(56) References Cited

U.S. PATENT DOCUMENTS
6,090,598 A    7/2000 Yamaguchi et al.

FOREIGN PATENT DOCUMENTS
| | | |
|---|---|---|
| CN | 1379795 A | 11/2002 |
| EP | 1 059 041 A1 | 12/2000 |
| EP | 1 486 569 A1 | 12/2004 |
| WO | WO 97/01632 | 1/1997 |
| WO | WO 97/01632 A1 | 1/1997 |
| WO | WO 01/14466 A1 | 3/2001 |

OTHER PUBLICATIONS

Broun et al., Catalytic plasticity of fatty acid modification enzymes underlying chemical diversity of plant lipids. Science, 1998, vol. 282: 1315-1317.*
Kisselev L., Polypeptide release factors in prokaryotes and eukaryotes: same function, different structure. Structure, 2002, vol. 10: 8-9.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
First Office Action CN200780049095.4 mailed May 2, 2012.

\* cited by examiner

*Primary Examiner* — Ganapathirama Raghu
(74) *Attorney, Agent, or Firm* — Steptoe & Johnson LLP

(57) ABSTRACT

There is provided a process for the preparation of a compound including the step of interesterifying in the presence of an enzyme catalyst (a) a first triglyceride compound and (b) a second triglyceride compound.

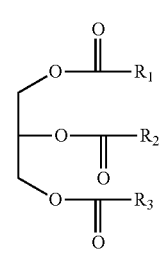

(I)

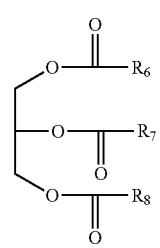

(II)

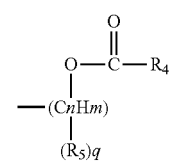

(III)

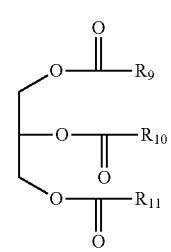

(IV)

20 Claims, No Drawings

PROCESS FOR PREPARING GLYCEROL ESTERS

CLAIM OF PRIORITY

This application claims priority under 35 USC 371 to International Application No. PCT/IB2007/004381, filed on Dec. 11, 2007, which claims priority to British Application Serial No. 0700074.8, filed on Jan. 3, 2007, each of which is incorporated by reference in its entirety.

The present invention relates to a process. In particular, the present invention relates to a process for preparing a compound which may act inter alia as a plasticiser and to a compound prepared by that process.

The manufacturing properties of thermoplastic polymers, for example the extruding properties of such polymers, is often modified/enhanced by the addition of plasticisers thereto. As acknowledged in the prior art, such as in U.S. Pat. No. 4,426,477, there is a tendency toward avoiding the commonly used plasticisers such as dioctyl adipate (DOA) and phthalate plasticisers such as dioctyl phthalate (DOP). The safety of these plasticisers has been called into question, particularly in certain applications.

U.S. Pat. No. 4,426,477 discloses plasticisers based on glycerol esters. The plasticisers consist of compounds prepared by the acylation of glycerol. The compounds comprises triesters, wherein approximately two of the acyls have two carbons and the remaining one acyl has from 10 to 14 carbons. The compounds of U.S. Pat. No. 4,426,477 provide a plasticising effect. However, in certain applications the plasticisers have a volatility such that they may migrate out of the thermoplastic polymer in which they are incorporated, such as PVC.

Our earlier application published as WO 01/14466 teaches a thermoplastic polymer composition containing a compound having the formula

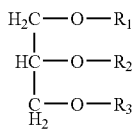

wherein $R_1$, $R_2$ and $R_3$ are independently selected from an acyl group or a hydrogen atom, wherein at least one of $R_1$, $R_2$ and $R_3$ is an acyl group (a short acyl group) having from 2 to 6 carbon atoms, and wherein at least one of $R_1$, $R_2$ and $R_3$ is a branched chain acyl group (a long acyl group) consisting of a saturated chain having 10 to 20 carbon atoms and a hydrophilic branch group.

WO 01/14466 discloses a process for the production of acylated monoglyceride of hydrogenated castor oil, which includes acylation of the hydrogenated castor oil with an acylation agent such as a short chain fatty acid anhydride followed by an interesterification of the acylated hydrogenated castor oil with a triacyl glycerol of a short chain fatty acid. The excess short chain tri acyl glycerol is removed and the product, an acylated monoglyceride of hydrogenated castor oil, is recovered. This process has some drawbacks due to the high temperature of about 250° C. involved during the interesterification of the acylated hydrogenated castor oil with the short chain triacyl glycerol. The high temperature can causes pyrolytic elimination of the short acyl group on the hydroxy fatty acid, leaving an unsaturated fatty acid, which reduces the stability of the product when incorporated into a thermoplastic polymer such as PVC. The present invention alleviates problems of the prior art.

Aspects of the invention are defined in the appended claims.

In one aspect the present invention provides a process for the preparation of a compound of the formula

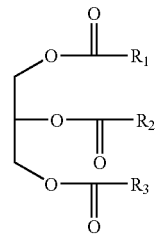

wherein one of $R_1$, $R_2$ and $R_3$ is selected from groups $R_6$, $R_7$ and $R_8$; wherein two of $R_1$, $R_2$ and $R_3$ are independently selected from groups $R_9$, $R_{10}$ and $R_{11}$; the process comprising the step of interesterifying in the presence of an enzyme catalyst (a) a triglyceride compound of the formula

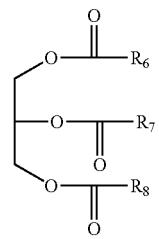

wherein each of $R_6$, $R_7$ and $R_8$ is independently selected from branched groups of the formula

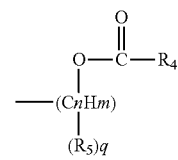

wherein q is from 0 to 3, wherein each $R_5$ is independently selected from —OH and —O—C(O)—$R_4$; wherein n is from 10 to 21 and m is selected from 2n-q, 2n-2-q, 2n-4-q, and 2n-6-q, wherein each $R_4$ is independently selected from alkyl, alkenyl and alkynyl groups containing z carbon atoms, wherein z is from 1 to 21, and (b) a triglyceride compound of the formula

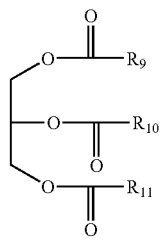

wherein each of $R_9$, $R_{10}$ and $R_{11}$ is independently selected from alkyl, alkenyl or alkynyl groups containing x carbon atoms, wherein each x is independently selected from 1 to 11.

Some Advantages

The present process overcomes the high temperature problems of WO01/14466. Moreover, the present process allows for the possibility of using different acyl groups on the hydrophilic branch group and on the glycerol backbone. This is possible in the processes described in the prior art.

For ease of reference, these and further aspects of the present invention are now discussed under appropriate section headings. However, the teachings under each section are not necessarily limited to each particular section.

Preferred Aspects

Enzyme

The enzyme for use in the process of the present may be any suitable enzyme capable of performing the required interesterification between the triglyceride compound of the formula

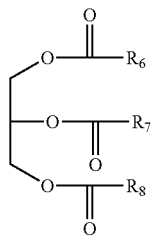

and the triglyceride compound of the formula

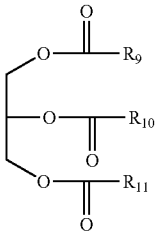

In one preferred aspect the enzyme is a lipase or protease.

Preferably the enzyme is a lipase and in particular the enzyme or the lipase is a 1,3 specific lipase. A preferred enzyme is Lipozyme TL IM available from Novozyme A/S, Denmark.

In one preferred aspect the enzyme is immobilised. The enzyme may be any suitable method, such as those described in EP-A-0407959 and include carrier bonding, crosslinking and inclusion. As an immobilizing carrier one may use those mentioned in EP-A-0407959, specifically, those inorganic materials such as active carbon, porous glass, acidic white clay, bleached white clay, kaolinite, alumina, silica gel, bentonite, hydroxyapatite, potassium phosphate and other metal oxides, natural polymeric compounds such as starch and gluten, synthetic polymeric materials such as polyethylene, polypropylen, phenol-formalin resin, acrylic resin, anionic exchange resin and cationic exchange resin. In particular, synthetic polymeric material having porosity as the physical form, for example, porous polyethylene, porous polypropylene, porous phenol formalin resin, porous acrylic resin. Various immobilizing carriers other than above may be used.

$R_1$ to $R_3$

As discussed herein one of $R_1$, $R_2$ and $R_3$ is selected from groups $R_6$, $R_7$ and $R_8$; and the other two of $R_1$, $R_2$ and $R_3$ are independently selected from groups $R_9$, $R_{10}$ and $R_{11}$. It will be understood by one skilled in the art and from the nature of an interesterification reaction that groups $R_1$, $R_2$ and $R_3$ are provided by 'donation' of groups from one triglyceride ester to another. Thus the compound prepare by the process of the present invention has its glycerol backbone provided by the triglyceride compounds provided from reaction in the process and the groups $R_1$, $R_2$ and $R_3$ are provided in part from one triglyceride and in part from the other triglyceride.

In one aspect $R_1$ is selected from groups $R_6$, $R_7$ and $R_8$; and $R_2$ and $R_3$ are independently selected from groups $R_9$, $R_{10}$ and $R_{11}$.

In one aspect $R_2$ is selected from groups $R_6$, $R_7$ and $R_8$; and $R_1$ and $R_3$ are independently selected from groups $R_9$, $R_{10}$ and $R_{11}$.

In one aspect $R_3$ is selected from groups $R_6$, $R_7$ and $R_8$; and $R_1$ and $R_2$ are independently selected from groups $R_9$, $R_{10}$ and $R_{11}$.

$R_6$ to $R_8$

As discussed herein each of $R_6$, $R_7$ and $R_8$ is independently selected from branched groups of the formula

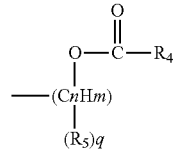

wherein q is from 0 to 3, wherein each $R_5$ is independently selected from —OH and —O—C(O)—$R_4$; wherein n is from 10 to 21 and m is selected from 2n-q, 2n-2-q, 2n-4-q, and 2n-6-q, wherein each $R_4$ is independently selected from alkyl, alkenyl and alkynyl groups containing z carbon atoms, wherein z is from 1 to 21.

q

It will be appreciated that q may be any of 0, 1, 2 or 3. In one aspect q is preferably 0. In one aspect q is preferably 1. In one aspect q is preferably 2. In one aspect q is preferably 3.

Integer q determines the number of $R_5$ groups attached to the CnHm moiety. It will be readily understood that the number of H i.e. the value of m will in some degree be determined by the number of $R_5$ groups i.e. the value of q.

$R_5$

As discussed herein each $R_5$ is independently selected from —OH and —O—C(O)—$R_4$; wherein n is from 10 to 21 and m is selected from 2n-q, 2n-2-q, 2n-4-q, and 2n-6-q, wherein each $R_4$ is independently selected from alkyl, alkenyl and alkynyl groups containing z carbon atoms, wherein z is from 1 to 21.

In one aspect at least one $R_5$ is —OH.

In one aspect each $R_5$ is —OH.

In one aspect at least one $R_5$ is —O—C(O)—$R_4$; wherein n is from 10 to 21 and m is selected from 2n-q, 2n-2-q, 2n-4-q, and 2n-6-q, wherein each $R_4$ is independently selected from alkyl, alkenyl and alkynyl groups containing z carbon atoms, wherein z is from 1 to 21.

In one aspect each $R_5$ is selected from —O—C(O)—$R_4$; wherein n is from 10 to 21 and m is selected from 2n-q, 2n-2-q, 2n-4-q, and 2n-6-q, wherein each $R_4$ is independently selected from alkyl, alkenyl and alkynyl groups containing z carbon atoms, wherein z is from 1 to 21.

In one aspect at least one $R_5$ is —OH and at least one $R_5$ is —O—C(O)—$R_4$; wherein n is from 10 to 21 and m is selected from 2n-q, 2n-2-q, 2n-4-q, and 2n-6-q, wherein each $R_4$ is independently selected from alkyl, alkenyl and alkynyl groups containing z carbon atoms, wherein z is from 1 to 21.

$R_4$

Each $R_4$ is independently selected from alkyl, alkenyl and alkynyl groups containing z carbon atoms, wherein z is from 1 to 21.

In one aspect at least one $R_4$ is independently selected from alkyl groups containing z carbon atoms, wherein z is from 1 to 21. In one aspect each $R_4$ is independently selected from alkyl groups containing z carbon atoms, wherein z is from 1 to 21.

In one aspect at least one $R_4$ is independently selected from alkenyl groups containing z carbon atoms, wherein z is from 1 to 21. In one aspect each $R_4$ is independently selected from alkenyl groups containing z carbon atoms, wherein z is from 1 to 21.

In one aspect at least one $R_4$ is independently selected from alkynyl groups containing z carbon atoms, wherein z is from 1 to 21. In one aspect each $R_4$ is independently selected from alkynyl groups containing z carbon atoms, wherein z is from 1 to 21.

z

In each aspect of the invention z is from 1 to 21. In one preferred aspect z is from 7 to 17. In one preferred aspect z is from 7 to 15. In one preferred aspect z is from 7 to 13. In one preferred aspect z is from 9 to 13. In one preferred aspect z is 11.

The or each z or at least one z may be different to at least one x. In one aspect the or each z is different to at least one x.

The or each z or at least one z may be different to each x. In one aspect the or each z is different to each x.

In one aspect the or each z or at least one z is equal to each. In one aspect the or each z is equal to each x.

n

As discussed herein n is from 10 to 21. Preferably n is from 15 to 21, for example n may be from 15 to 19. Preferably n is 17.

m

The integer m is selected from 2n-q, 2n-2-q, 2n-4-q, and 2n-6-q. It will be appreciated that the value of m will depend on the number of 'spare' valencies on the n number of carbons. The group CnHm may be saturated (2n-q), contain one degree of unsaturation (2n-2-q), contain two degrees of unsaturation (2n-4-q), or contain three degrees of unsaturation (2n-6-q). When the group CnHm contains degrees of unsaturation this may be in the form of C=C bonds, C≡C bonds or a combination thereof.

$R_9$ to $R_{11}$

As discussed herein each of $R_9$, $R_{10}$ and $R_{11}$ is independently selected from alkyl, alkenyl or alkynyl groups containing x carbon atoms, wherein each x is independently selected from 1 to 11.

In one aspect at least one of $R_9$, $R_{10}$ and $R_{11}$ is independently selected from alkyl groups containing x carbon atoms, wherein each x is independently selected from 1 to 11. In one aspect each of $R_s$, $R_{10}$ and $R_{11}$ is independently selected from alkyl groups containing x carbon atoms, wherein each x is independently selected from 1 to 11.

In one aspect at least one of $R_9$, $R_{10}$ and $R_{11}$ is independently selected from alkenyl groups containing x carbon atoms, wherein each x is independently selected from 1 to 11. In one aspect each of $R_9$, $R_{10}$ and $R_{11}$ is independently selected from alkenyl groups containing x carbon atoms, wherein each x is independently selected from 1 to 11.

In one aspect at least one of $R_9$, $R_{10}$ and $R_{11}$ is independently selected from alkynyl groups containing x carbon atoms, wherein each x is independently selected from 1 to 11.

In one aspect each of $R_9$, $R_{10}$ and $R_{11}$ is independently selected from alkynyl groups containing x carbon atoms, wherein each x is independently selected from 1 to 11.

x

Each x is independently selected from 1 to 11.

In one preferred aspect at least one x is independently selected from 1 to 5. Preferably each x is independently selected from 1 to 5.

In one preferred aspect at least one x is independently selected from 1 to 3. Preferably each x is independently selected from 1 to 3.

In one preferred aspect at least one x is 1. Preferably each x is 1.

In one aspect each x is the same.

Preferred Aspects

In one highly preferred aspect of the present invention each x is 1 and z is 11.

In one highly preferred aspect of the present invention each x is 1, n is 17 and z is 1.

In one highly preferred aspect of the present invention a compound selected from

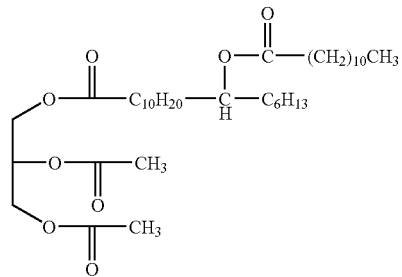

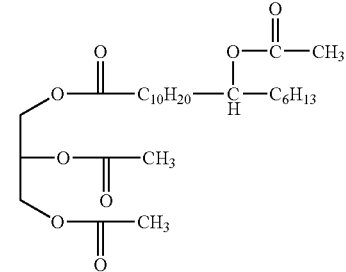

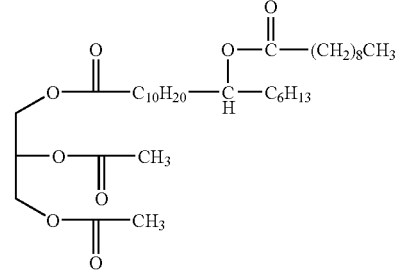

The present invention will now be described in further detail in the following examples.

EXAMPLES

Enzymatic production of acetylated monoglyceride of hydrogenated castor oil.

Example 1

Lab journal No.: 2410/53 TLJ
Materials:
Acetylated hydrogenated castor oil (TAC HCAO lot. no. 2332/121)
Triacetin, item no. 021652, lot. no. 4010172485
1.) Lipozyme TL IM, Novozymes, lot. No. LA35000405
2.) Lipozyme TL IM, Novozymes, lot. No. LA350012
3.) Lipozyme TL IM, Novozymes, lot. No. LA35002001
Lipase QLG, Meito Sangyo co., ltd, lot. No. QG9401
Lipase PLG, Meito Sangyo co., ltd, lot. No. PG OX01
Lipase QLC, Meito Sangyo co., ltd, lot. no. QC3Z01
Lipase PLC, Meito Sangyo co., ltd, lot. No. PC2301
Lipase PS-D "Amano" I, Amano Enzymes, Inc, lot. No. ILPSAB015235R
Lipase PS-C "Amano" II, Amano Enzymes, Inc, lot. No. ILPSAC0252304R
Lipase PS-C "Amano" I, Amano Enzymes, Inc, lot. No. ILPSAA0550903R TAC HCAO, Triacetin and enzyme was mixed in 20 mL Wheaton glasses. The samples were placed in a heating block at 60° C., with magnetic stirring. After 48 hours the reaction was stopped. The enzyme was removed by filtration. Samples were analyzed using gas chromatography (GC)

fittings were made with Swagelok fittings. Rockwool with a layer of aluminium foil on the outside was used as insulation of the pipes.

Dimension of the reactor was:

Diameter outside: 25 mm

Diameter inside: 22 mm

Length: 770 mm

The reactor had a heated jacket. Dimension was:

Diameter outside: 38 mm

Length: 400 mm

Example 2

Dewatering of Enzyme Bed

The enzyme contains some water and to prevent hydrolysis and thereby formation of free fatty acids during reaction, the enzyme was dewatered. The dewatering was done by flushing the enzyme with TAC HCAO. The product from the dewatering was collected but was treated as waste.

| Lab journal no. | TAC HCAO [gram] | Triacetin [gram] | Enzyme | Enzyme (g) | % MONO-2AC-18OAC |
|---|---|---|---|---|---|
| 2410/53-1 | 1.1088 | 0.674 | 1.) Lipozyme TL IM | 0.1683 | 30.6 |
| 2410/53-2 | 1.1089 | 0.6358 | 2.) Lipozyme TL IM | 0.1669 | 29.2 |
| 2410/53-3 | 1.1072 | 0.6532 | 3.) Lipozyme TL IM | 0.1664 | 31.2 |
| 2410/53-4 | 1.0476 | 0.6645 | Lipase QLG | 0.1619 | 37.8 |
| 2410/53-5 | 1.0491 | 0.6757 | Lipase PLG | 0.1864 | 35.1 |
| 2410/53-6 | 1.0863 | 0.7789 | Lipase QLC | 0.1745 | 35.8 |
| 2410/53-7 | 1.0684 | 0.6899 | Lipase PLC | 0.1678 | 32.6 |
| 2410/53-8 | 1.0729 | 0.6942 | Lipase PS-D "Amano"I | 0.1703 | 31.5 |
| 2410/53-9 | 1.0431 | 0.6314 | Lipase PS-C "Amano"II | 0.1721 | 35 |
| 2410/53-10 | 1.0683 | 0.6657 | Lipase PS-C "Amano"I | 0.1767 | 35.3 |

% MONO-2AC-18OAC is defined as weight % of the total sample of the group of molecules consisting of 12-acetyloxy-octadecanoic acid 2,3-bis-acetyloxy-propyl ester Mw = 500.67 gram/mol and 12-acetyloxy-octadecanoic acid 1,3-bis-acetyloxy-prop-2-yl ester Mw = 500.67 gram/mol.

Example 2-6

Continuous Flow Reactions in Enzyme Bed

Equipment

Reactor, heat exchanger and packed bed enzyme reactor:

The reactor, heat exchanger and packed bed enzyme reactor were made of pipes of stainless steel. All connections and Lab journal No.: 2381/138
Materials:
TAC HCAO, 2332/121 POA
Lipozyme TL IM, LA3500012

80.0 g of enzyme (dry powder) was packed into the reactor. TAC HCAO was pumped though the reactor, and samples were collected. The acid value expressed as mg KOH used to neutralise the free fatty acids in 1 gram of sample (AV) was determined by titration.

| Journal no. | Time | Pump setting | Set point (° C.) | Temp. Heat exchanger (° C.) | Temp. Reactor (° C.) | Pressure (bar) | Flow (g/h) | AV (mg KOH/g sample) |
|---|---|---|---|---|---|---|---|---|
| 2381/139-1 | 11.10 | 5 | 60 | 55 | 30 | 2.3 | 431 | 35 |
| 2381/139-2 | 11.30 | 5 | 65 | 59 | 50 | 2.022 | 420 | 19.7 |
| 2381/139-3 | 12.45 | 5 | 65 | 60 | 56 | 1.974 | 430 | 4.5 |
| 2381/139-4 | 13.45 | 5 | 65 | 60 | 55 | 1.905 | 439 | 3.2 |
| 2381/139-5 | 14.00 | 2 | 65 | 60 | 55 | 1.990 | 146 | 2.2 |

The dewatered enzyme packed bed reactor was used as reactor in example 3,4 and 5.

Example 3

Conversion of TAC HCAO and Triacetin Molar Ratio 1:3

Three different flow rates was investigated
Lab journal No.: 2381/140-2381/141, 2410/1-2410/2
Material:
TAC HCAO, 2332/121 POA
Triacetin, item no. 021652, lot. no. 4010172485
Lipozyme TL IM, LA3500012
10.34 kg TAC HCAO and 6.50 kg Triacetin (TAC HCAO/Triacetin molar ratio 1:3) was mixed in a 25 L metal container. Pump setting 1, 2 and 4 were investigated, the flow rate was measured and the conversion was determined by GC analysis.

| Sample no. | Time (h) | Temp. Heat exchanger (° C.) | Temp. Reactor (° C.) | Pressure (bar) | Pump setting | Flow (g/h) | Feed (kg) | MONO-2AC-18OAC |
|---|---|---|---|---|---|---|---|---|
| 2381/140-1 | 19 | 21 | 24 | 1.408 | 1 | 71 | 1.72 | 31.3 |
| 2381/140-2 | 2.75 | 55 | 50 | 1.149 | 2 | 183.5 | 0.58 | 20.8 |
| 2381/140-3 | 1.67 | 58 | 53 | 1.306 | 4 | 361.7 | 0.74 | 33.3 |
| 2381/141-1 | 3.83 | 51 | 42 | 1.06 | 1 | 92.1 | 0.28 | 29.8 |
| 2381/141-2 | 23.9 | 52 | 43 | 1.166 | 1 | 91.7 | 2.16 | 15.1 |

Example 4

Conversion of TAC HCAO and Triacetin Molar Ratio 1:2

Three different flow rates was investigated
Lab journal No.: 2410/1
Materials:
TAC HCAO, 2332/121 POA
Triacetin, item no. 021652, lot. no. 4010172485
Lipozyme TL IM, Batch LA350012
3.1998 kg TAC HCAO and 1.3020 kg Triacetin was mixed in a 10 L metal container. Pump setting 1, 2 and 4 were investigated, the flow rate was measured and the conversion was determined by GC analysis.

| Sample no. | Time (h) | Temp. Heat exchanger (° C.) | Temp. Reactor (° C.) | Pressure (bar) | Pump setting | Flow (g/h) | MONO-2AC-18OAC |
|---|---|---|---|---|---|---|---|
| 2410/1-1 | 2.25 | 55 | 47 | 1.12 | 2 | 177.4 | 24.2 |
| 2410/1-2 | 19.5 | 51 | 43 | 1.201 | 1 | 87.6 | 12.4 |
| 2410/1-3 | 1.5 | 58 | 52 | 1.32 | 4 | 338.4 | 19 |

Example 5

Conversion of TAC HCAO and Triacetin Molar Ratio 1:5

Three different flow rates was investigated
Lab journal No.: 2410/2
Material: TAC HCAO, 2332/121 POA
Triacetin, item no. 021652, lot. no. 4010172485
Lipozyme TL IM, Batch LA350012
2.1366 kg TAC HCAO and 2.1906 kg Triacetin was mixed in a 10 L metal container.
Pump setting 1, 2 and 4 were investigated, the flow rate was measured and the conversion was determined by GC analysis.

| Sample no. | Time (h) | Temp. Heat exchanger (° C.) | Temp. Reactor (° C.) | Pressure (bar) | Pump setting | Flow (g/h) | MONO-2AC-18OAC |
|---|---|---|---|---|---|---|---|
| 2410/2-1 | 3 | 56 | 48 | 1.095 | 2 | 170.7 | 20.3 |
| 2410/2-2 | 17.25 | 51 | 42 | 1.097 | 1 | 76.1 | 6.8 |
| 2410/2-3* | 1.75 | 58 | 53 | 1.297 | 4 | 370.4 | 7.1 |

*The sample was not homogeneous

Example 6

Distillation of Product

Lab journal No.: 2314/121 HV, 2314/122 HV
Material:
2410/5 TLJ a mixture of 2381/140-2 and 2381/140-3, products of experiment 3

The distillation was made in two steps. In step 1 Triacetin was removed by water vapour distillation. 1264 g sample were water vapour distilled at 180° C. in 45 min at <0.5 mbar. Yield was 857 g.

In step 2 the product from step 1 was distilled on a short path distiller. 729 g sample was distilled at 230° C. at 0.6 Pa. The yield was 329 g. The product was analysed on GC and acid value and colour was measured.

Analytical Results:
A334/ST 315 3461/22 IP

| | Sample before distillation | Sample after removing Triacetin | Destillation product |
|---|---|---|---|
| % Triacetin | 32.2 | 0.0 | 0.0 |
| % FFA-18 | 0.2 | 0.2 | 0.2 |
| % FFA-18 OAC | 0.1 | 0.1 | 0.7 |
| % MONO-AC | 0.1 | 0.2 | 0.4 |
| % MONO-2AC | 2.7 | 4.5 | 9.9 |
| % MONO-2AC 18OH | 0.3 | 0.5 | 0.9 |
| % MONO-2AC 18OAC | 24.8 | 36.0 | 79.5 |
| % DI-AC | n.c. | n.c. | 4.3 |
| % TRI | n.c. | n.c. | 0.2 |
| % Total | | | 96.2 | n.c. = not calculated

| Acid Value | 2.2 meq KOH/g sample |
|---|---|
| Lovibond Colour 5¼" | Total = 1.2<br>Red = 0.8<br>Yellow = 3.6 |

Examples 7-12

Raw Materials and Solvents

| Raw material | Manufacturer | Lot |
|---|---|---|
| Hydrogenated castor oil | Oleo Chemie | A/288/02 |
| Acetic acid anhydride | | |
| Dodecanoyl chloride | Acros Organics | A013306701 |
| Decanoyl chloride | | 1299606-4010171740 |
| Pyridine | | |
| Methylene chloride | | |
| Demineralised water | | |
| Mg-sulphate | | |
| Lipozyme TL IM | Novozyme A/S | La350012 |

Example 7

Preparation of acetylated hydrogenated castor oil from a mixture of hydrogenated castor oil and acetic acid anhydride.

Equipment:

50 L stainless steel reactor with electrical heating, mechanical stirring, water vapour supply, distillation column, condenser, distillate collector and vacuum equipment.

Experiment:

24 kg hydrogenated castor oil flakes were added to the reactor together with 8.4 kg acetic acid anhydride and heated to 80° C. where the stirring was turned on. The reaction started at 120° C. and the temperature allowed to rise.

Example 8

Preparation of acylated hydrogenated castor oil from a mixture of hydrogenated castor oil and dodecanoyl chloride in methylene chloride using pyridine as a catalyst.

Equipment:

5000 mL three necked reaction flask equipped with temperature control, reflux condenser, mechanical stirrer, pressure equalising dosing funnel, nitrogen supply and drying tube. 5000 mL separation funnel, filtration equipment and rotary evaporator.

Experiment:

275 gram of hydrogenated castor oil was dissolved in 2400 mL dry methylene chloride (kept dry over molecular sieve) at 40° C. The solution was cooled to 30° C. and 62 gram of pyridine was added. 169 gram of dodecanoyl chloride was dissolved in 250 mL dry methylene chloride and added to the dosing funnel. The dodecanoyl chloride solution was added slowly to the reaction mixture during 3 hours keeping the temperature at 30° C.

To the reaction mixture was added 600 mL 30° C. warm demineralised water and the mixture was separated in the separation funnel. The organic phase was washed twice with additional 600 mL 30° C. warm demineralised water. The organic phase was kept at 30° C. and dried with Mg-sulphate.

The dry organic phased was filtered and concentrated in a rotary evaporator at 40° C. and 30 kPa for 30 min and 70° C. for 30 min.

Yield 439 gram of 1,2,3-tri-(12-dodecanoyloxy-octadecanoyloxy)-propane (Mw: 1486.39 gram/mol)

Example 9

Drying of immobilised enzyme preparation of *Thermomyces lanuginosa* lipase Lipozyme TL IM (Novozyme A/S) with acetylated hydrogenated castor oil (1,2,3-tri-(12-acetylxy-octadecanoyloxy)-propane)

Equipment:

3000 mL three necked reaction flask with temperature control, mechanical stirrer and nitrogen cover.

Experiment:

1054 gram of acetylated hydrogenated castor oil was placed in the reactor with 147 gram of Lipozyme TL IM and heated to 60° C. for 24 hrs in order to hydrolyse the (12-acetyloxy-ocatadecanoic acid moieties from the glycerol backbone using the water which was added with the enzyme (water content of the enzyme was about 7%).

The reaction mixture was decanted from the enzyme, and the enzyme was used in example 3 and 5.

Example 10

Interesterification of triacetin with 1,2,3-tri-(12-dodecanoyloxy-octadecanoyloxy)-propane (product of example 8) using the dried enzyme of example 9 as catalyst, removal of excess triacetin and recover of the main product 12-dodecanoyloxy-ocatadecanoic acid 2,3-bis(acetoxy)-propyl ester (Mw: 640.93 gram/mol) and its positional isomer 12-dodecanoyloxy-octadecanoic acid 2-acetoxy-1-acetoxymethyl-ehtyl ester (Mw. 640.93 gram/mol) (LODA)

Equipment:

3000 mL three necked reaction flask with temperature control, mechanical stirrer and nitrogen cover. 5000 mL distillation equipment with Claissen head, water vapour addition tube and vacuum equipment, Filtration equipment and molecular distillation equipment (KDL 5 from UIC Gmbh.)

Experiment:

Three reactions with 1000 gram of 1,2,3-tri-(12-dodecanoyloxy-octadecanoyloxy)-propane (product of example 8) was placed in the reactor and mixed with the dried enzyme of example 2 and 470 gram of triacetin was added. The reactor was heated to 60° C. and reacted for 24 hours. The enzyme was removed by filtration and the reaction mixture was placed in a 5000 mL distillation equipment and heated to 180° C. at reduced pressure of 0.2 kPa with water vapour addition for 1.5 hours to remove excess triacetin from the reaction mixture. 2623 gram of a concentrated reaction mixture was treated in a molecular distillation equipment at 255° C., 0.7 Pa and a flow of 786 gram/hour. 1346 gram or 51.3% was recovered as distillate. The enzyme from Example 12 was reused in the following reaction.

The distillate was analysed by gas chromatography (GC) and consist of 56 weight % of a mixture of 12-dodecanoyloxy-ocatadecanoic acid 2,3-bis(acetoxy)-propyl ester (Mw: 640.93 gram/mol) and its positional isomer 12-dodecanoyloxy-octadecanoic acid 2-acetoxy-1-acetoxymethyl-ehtyl ester (Mw: 640.93 gram/mol) in the ration 2:1.

Example 11

Preparation of acylated hydrogenated castor oil from a mixture of hydrogenated castor oil and decanoyl chloride in methylene chloride using pyridine as a catalyst.

Equipment:

5000 mL three necked reaction flask equipped with temperature control, reflux condenser, mechanical stirrer, pressure equalising dosing funnel, nitrogen supply and drying tube. 5000 mL separation funnel, filtration equipment and rotary evaporator.

Experiment:

275 gram of hydrogenated castor oil was dissolved in 2300 mL dry methylene chloride (kept dry over molecular sieve) at 40° C. The solution was cooled to 30° C. and 62 gram of pyridine was added. 148 gram of decanoyl chloride was dissolved in 250 mL dry methylene chloride and added to the dosing funnel. The decanoyl chloride solution was added slowly to the reaction mixture during 3 hours keeping the temperature at 38° C.

The reaction mixture was added 600 mL 30° C. warm demineralised water and the mixture was separated in the separation funnel. The organic phase was washed twice with additional 600 mL 30° C. warm demineralised water. The organic phase was kept at 30° C. and dried with Mg-sulphate.

The dry organic phased was filtered and concentrated in a rotary evaporator at 40° C. and 30 kPa for 30 min and 70° C. for 30 min.

Yield 415 gram of 1,2,3-tri-(12-decanoyloxy-octadecanoyloxy)-propane (Mw: 1402.23 gram/mol)

Example 12

Interesterification of triacetin with 1,2,3-tri-(12-decanoyloxy-octadecanoyloxy)-propane (product of example 11) using the dried enzyme of example 2 as catalyst, removal of excess triacetin and recover of the main product 12-decanoyloxy-ocatadecanoic acid 2,3-bis(acetoxy)-propyl ester (Mw: 612.88 gram/mol) and its positional isomer 12-decanoyloxy-octadecanoic acid 2-acetoxy-1-acetoxymethyl-ehtyl ester (Mw. 612.88 gram/mol) (DODA)

Equipment:

3000 mL three necked reaction flask with temperature control, mechanical stirrer and nitrogen cover. 5000 mL Distillation equipment with Claissen head, water vapour addition tube and vacuum equipment, filtration equipment and molecular distillation equipment (KDL 5 from UIC Gmbh.)

Experiment:

Three reactions with 1000 gram of 1,2,3-tri-(12-decanoyloxy-octadecanoyloxy)-propane (product of example 11) was placed in the reactor and mixed with the used enzyme of example 10 and 470 gram of triacetin was added. The reactor was heated to 60° C. and reacted for 24 hours. The enzyme was removed by filtration and the reaction mixture was placed in a 5000 mL distillation equipment and heated to 180° C. at reduced pressure of 0.2 kPa with water vapour addition for 1.5 hours to remove excess triacetin from the reaction mixture. 2623 gram of a concentrated reaction mixture was treated in a molecular distillation equipment at 255° C., 0.7 Pa and a flow of 786 gram/hour. 1346 gram or 51.3% was recovered as distillate.

The distillate was analysed by GC and consist of 71 weight % of a mixture of 12-decanoyloxy-ocatadecanoic acid 2,3-bis(acetyloxy)-propyl ester (Mw: 612.88 gram/mol) and its positional isomer 12-decanoyloxy-octadecanoic acid 2-acetyloxy-1-acetoxymethyl-ehtyl ester (Mw. 612.88 gram/mol) in the ration 2:1.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

The invention claimed is:

1. A process for the preparation of a compound of the formula

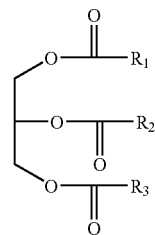

wherein one of $R_1$, $R_2$ and $R_3$ is selected from groups $R_6$, $R_7$ and $R_8$ wherein two of $R_1$, $R_2$ and $R_3$ are independently selected from groups $R_9$, $R_{10}$ and $R_{11}$ the process comprising the step of interesterifying in the presence of a lipase (a) a triglyceride compound of the formula

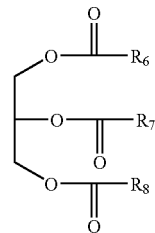

wherein each of $R_6$, $R_7$ and $R_8$ is independently selected from branched groups of the formula

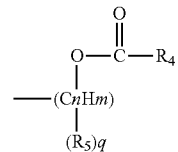

wherein q is from 0 to 3, wherein each $R_5$ is independently selected from —OH and —O—C(O)—$R_4$ wherein n is from 10 to 21 and m is selected from 2n-q, 2n-2-q, 2n-4-q, and 2n-6-q, wherein each $R_4$ is independently selected from alkyl, alkenyl and alkynyl groups containing z carbon atoms, wherein z is from 1 to 21, and (b) a triglyceride compound of the formula

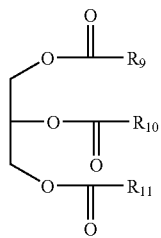

wherein each of $R_9$, $R_{10}$ and $R_{11}$ is independently selected from alkyl, alkenyl or alkynyl groups containing x carbon atoms, wherein each x is independently selected from 1 to 5.

2. A process according to claim 1 wherein the lipase is a 1,3 specific lipase.

3. A process according to claim 1 wherein z is different to at least one x.

4. A process according to claim 1 wherein each x is the same.

5. A process according to claim 1 wherein z is different to each x.

6. A process according to claim 1 wherein z and each x are equal.

7. A process according to claim 1 wherein each x is independently selected from 1 to 3.

8. A process according to claim 1 wherein each x is 1.

9. A process according to claim 1 wherein n is from 15 to 21.

10. A process according to claim 1 wherein n is from 15 to 19.

11. A process according to claim 1 wherein n is 17.

12. A process according to claim 1 wherein z is from 7 to 17.

13. A process according to claim 1 wherein z is from 7 to 15.

14. A process according to claim 1 wherein z is from 9 to 13.

15. A process according to claim 1 wherein z is 11.

16. A process according to claim 1 wherein each x is 1 and z is 11.

17. A process according to claim 1 wherein each x is 1, n is 17 and z is 1.

18. A process according to claim 1 wherein the compound is of the formula

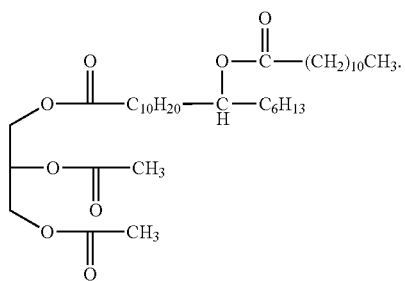

19. A process according to claim 1 wherein the compound is of the formula

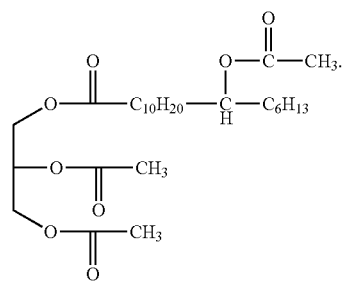

20. A process according to claim 1 wherein the compound is of the formula

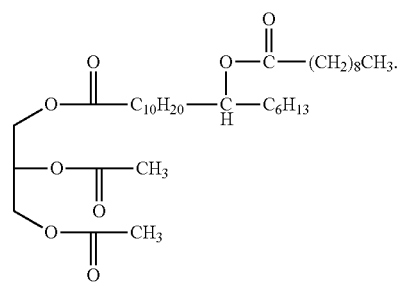

* * * * *